(12) United States Patent  (10) Patent No.: US 8,738,153 B2
Sage et al.  (45) Date of Patent: May 27, 2014

(54) IMPLANTABLE LEAD WITH BRAIDED CONDUCTORS

(71) Applicant: Greatbatch Ltd., Clarence, NY (US)

(72) Inventors: Shahn S. Sage, Andover, MN (US);
John M. Swoyer, Blaine, MN (US);
Jesse Geroy, Ham Lake, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/019,653

(22) Filed: Sep. 6, 2013

(65) Prior Publication Data

US 2014/0012357 A1 Jan. 9, 2014

Related U.S. Application Data

(62) Division of application No. 13/045,908, filed on Mar. 11, 2011, now Pat. No. 8,543,223.

(51) Int. Cl.
*A61N 1/04* (2006.01)

(52) U.S. Cl.
USPC ............ 607/116; 600/377; 607/117; 607/122

(58) Field of Classification Search
None
See application file for complete search history.

(56) References Cited

U.S. PATENT DOCUMENTS

| | | | |
|---|---|---|---|
| 5,643,330 A | 7/1997 | Holsheimer et al. | |
| 6,249,707 B1 | 6/2001 | Kohnen et al. | |
| 6,308,103 B1 | 10/2001 | Gielen | |
| 6,968,237 B2 | 11/2005 | Doan et al. | |
| 7,792,591 B2 | 9/2010 | Rooney et al. | |
| 7,797,057 B2 | 9/2010 | Harris | |
| 7,798,864 B2 | 9/2010 | Barker et al. | |
| 7,831,311 B2 | 11/2010 | Cross et al. | |
| 2006/0089696 A1 | 4/2006 | Olsen et al. | |
| 2007/0168007 A1 | 7/2007 | Kuzma et al. | |
| 2008/0147155 A1 | 6/2008 | Swoyer et al. | |
| 2009/0005844 A1 | 1/2009 | Swoyer et al. | |
| 2009/0099441 A1 | 4/2009 | Giszter et al. | |
| 2009/0270957 A1 | 10/2009 | Pianca et al. | |
| 2010/0042109 A1 | 2/2010 | Barker | |
| 2010/0070012 A1 | 3/2010 | Chinn et al. | |
| 2010/0312319 A1 | 12/2010 | Barker | |

*Primary Examiner* — Brian T Gedeon
*Assistant Examiner* — Ankit Tejani
(74) *Attorney, Agent, or Firm* — Michael P. Horvath

(57) ABSTRACT

In some examples, an extension includes a connector adapted to electrically couple to a proximal end of the therapy delivery element. An elongated extension body is attached to the connector. The elongated extension body includes a stylet coil having a stylet coil lumen. The stylet coil extends within the elongated extension body to the connector. A conductor assembly includes a plurality of insulated electrical conductors braided to extend around the stylet coil and electrically coupled to the connector. The conductor assembly includes an inner lumen with a diameter greater than an outside diameter of the stylet coil, wherein axial elongated of the elongated extension body reduces the inner diameter of the conductor assembly. A low durometer insulator extends around the conductor assembly. A stylet is sized to slide freely within the stylet coil lumen during implantation of the extension in the living body.

20 Claims, 8 Drawing Sheets

IMPLANTABLE LEAD WITH BRAIDED CONDUCTORS

CLAIM OF PRIORITY

This application is a divisional of and claims the benefit of priority under 35 U.S.C. §120 to Sage et al., U.S. patent application Ser. No. 13/045,908, now U.S. Pat. No. 8,543,223, entitled "IMPLANTABLE LEAD WITH BRAIDED CONDUCTORS", filed on Mar. 11, 2011, which is incorporated by reference herein in its entirety.

FIELD

The present disclosure relates to a therapy delivery element with braided electrical conductors that permit elongation of the elongated lead body without damage to the conductors.

BACKGROUND

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Peripheral Nerve Stimulation (PNS) systems have demonstrated efficacy in the treatment of chronic pain syndromes and incontinence, and a number of additional applications are currently under investigation. Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more therapy delivery elements implanted at the desired stimulation site and an implantable neurostimulator, such as an implantable pulse generator (IPG), implanted remotely from the stimulation site, but coupled either directly to the therapy delivery elements or indirectly to the therapy delivery elements via one or more extensions in cases where the length of the therapy delivery elements is insufficient to reach the IPG. In some cases, the extension leads may be used to facilitate coupling of the neurostimulator, which may otherwise be incompatible with the therapy delivery elements or extension leads, thereto. Thus, electrical pulses can be delivered from the neurostimulator to the therapy delivery elements to stimulate the tissue and provide the desired efficacious therapy to the patient.

In the context of an SCS procedure, one or more therapy delivery elements are introduced through the patient's back into the epidural space under fluoroscopy, such that the electrodes carried by the leads are arranged in a desired pattern and spacing to create an electrode array. The specific procedure used to implant the therapy delivery elements will ultimately depend on the type of therapy delivery elements used. Currently, there are two types of commercially available therapy delivery elements: a percutaneous lead and a surgical lead.

A percutaneous lead includes a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline. In many cases, a stylet, such as a metallic wire, is inserted into a lumen running through the center of each of the percutaneous leads to aid in insertion of the lead through the needle and into the epidural space. The stylet gives the lead rigidity during positioning, and once the lead is positioned, the stylet can be removed after which the lead becomes flaccid.

As a patient implanted with a therapy delivery element moves, some regions of the body may expand and contract, resulting in changes in length. The movement may exert high loading forces on anchors, therapy delivery elements, lead extensions, or body tissue. These forces may cause lead failure, axial migration of electrodes, anchor damage, or tissue damage. The patient may experience pain or operational failure or performance degradation of the therapy delivery elements.

U.S. Pat. No. 7,831,311 (Cross, et al.) is directed to implantable leads with a lead body construction designed to accommodate loading forces exerted on the lead body during patient movement. The lead body is sufficiently stretchable to resist forces that could otherwise cause lead failure, axial migration of the electrodes, anchor damage, or tissue damage. The lead body may include a variety of features that reduce the axial stiffness of the lead without significantly impacting the operation and structural integrity of lead components, such as electrodes, conductors and insulators. For example, a lead body may include a low durometer outer jacket and/or conductors with a low modulus of elasticity, providing increased stretchability. Increasing stretchability of a lead body can also increase the vulnerability of the lead body to flex fatigue, buckling fatigue, kinking, and crush. In some embodiments, the lead may also include a coiled wire stylet guide to provide enhanced column strength. The coiled wire stylet guide may or may not be electrically conductive.

BRIEF SUMMARY

The present disclosure is directed to a therapy delivery element adapted to be implanted into a living body. The therapy delivery element includes an electrode portion with a plurality of electrodes. At least one elongated lead body is attached to the electrode portion. The elongated lead body includes a stylet coil having a stylet coil lumen. The stylet coil extends within the elongated lead body and along at least a portion of the electrode portion. A conductor assembly with a plurality of insulated electrical conductors is braided to extending around the stylet coil and to electrically couple to one or more of the electrodes. The conductor assembly includes an inner lumen with a diameter greater than an outside diameter of the stylet coil. Axial elongation of the elongated lead body reduces the inner diameter of the conductor assembly. A low durometer insulator extends around the conductor assembly. A stylet sized to slide freely within the stylet coil lumen is provided for use during implantation of the therapy delivery element into the living body.

The electrode portion can be a paddle electrode or a ring electrode. A plurality of elongated lead bodies can be attached to the electrode portion. The stylet coil preferably extends substantially to the distal end of the electrode portion. The stylet coil is preferably a helical coil. The stylet coil deforms elastically in response to axial elongation of the elongated lead body.

Axial elongation of the braided electrical conductors displaced the electrical conductors toward alignment with central axis of the elongated body portion. There is a gap between the stylet coil and the inner lumen of the conductor assembly when the elongated lead body is in a relaxed condition. The gap permits the conductor assembly to neck-down during elongation. The elongated lead body preferably has an axial stiffness that permits an axial elongation of at least 10% to approximately 35% without breakage of the electrical conductors. The low durometer insulator preferably has a durometer in a range of about 55 Shore A to about 75 Shore A.

The present disclosure is also directed to a neurostimulation system including an implantable pulse generator and a therapy delivery element according to an embodiment of the present disclosure. A stylet sized that slides freely within the stylet coil lumen is provided for use during implantation of the therapy delivery element into the living body.

The present disclosure is also directed to an extension for therapy delivery element. The extension includes a connector adapted to electrically couple to a proximal end of the therapy delivery element and an elongated extension body attached to the connector. The elongated extension body includes a stylet coil having a stylet coil lumen. The stylet coil extends within the elongated extension body to the connector. A conductor assembly including a plurality of insulated electrical conductors is braided to extending around the stylet coil and electrically coupled to the connector. The conductor assembly includes an inner lumen with a diameter greater than an outside diameter of the stylet coil, wherein axial elongated of the elongated extension body reduces the inner diameter of the conductor assembly. A low durometer insulator preferably extends around the conductor assembly. A stylet is provided that is sized to slide freely within the stylet coil lumen during implantation of the extension in the living body.

The present disclosure is also directed to method of implanting therapy delivery elements in a living body. The method includes inserting a stylet in a lumen of a stylet coil extending through an elongated lead body of the therapy delivery element. The stylet coil is surrounded by a conductor assembly including a plurality of electrical conductors braided to form a generally tubular structure electrically coupled to one or more of electrodes at a distal end of the therapy delivery element. The stylet adds stiffness to elongated lead body during positioning of the therapy delivery element in the living body. The stylet is removed from the therapy delivery element, rendering the elongated lead body flaccid. The electrical conductors at a proximal end of the elongated lead body are electrically coupled to an implantable pulse generator implanted in the living body. An inner diameter of the conductor assembly is reduced in response to axial elongation of the elongated body portion.

The method includes displacing the electrical conductors toward alignment with a central axis of the in response to axial elongation.

DETAILED DESCRIPTION OF SOME EMBODIMENTS

The description that follows relates to spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
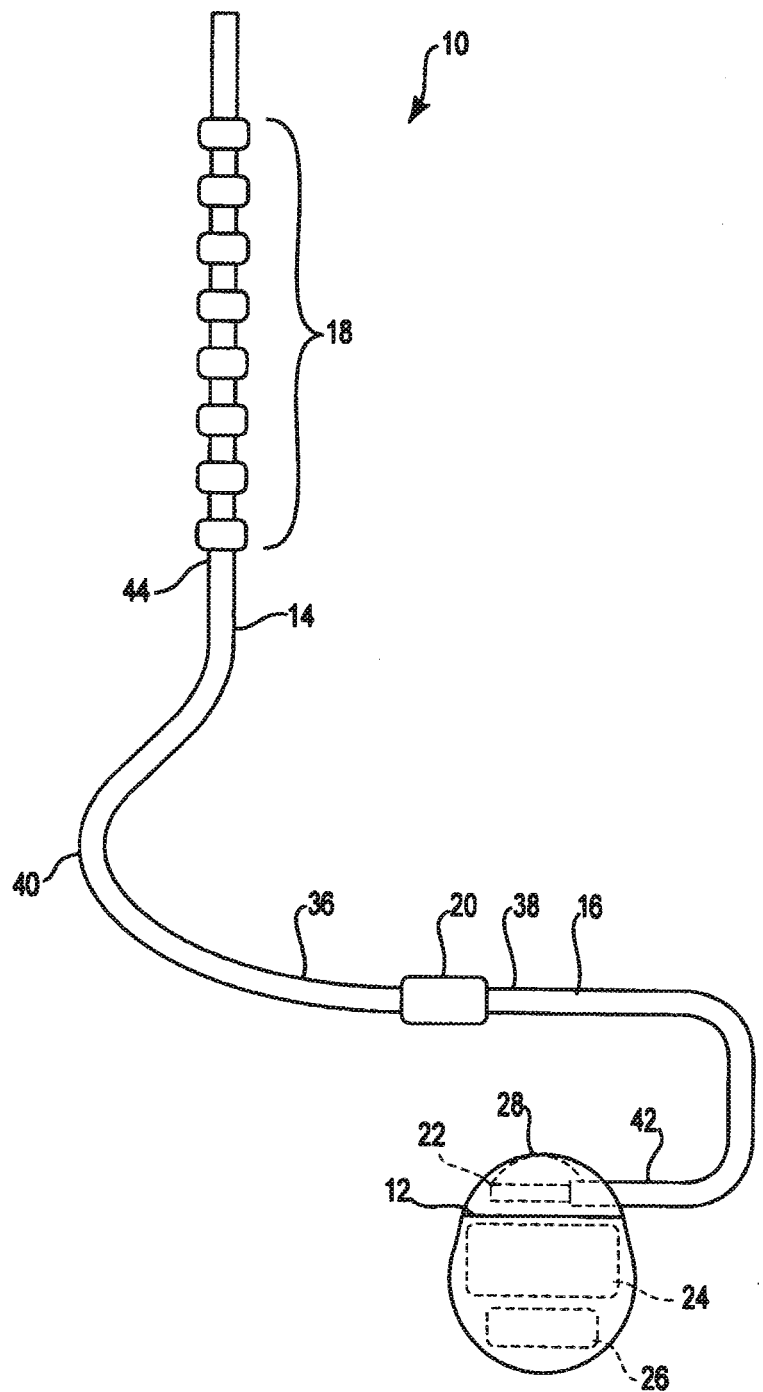
FIG. 1 is a schematic illustration of a therapy delivery system.

FIGS. 1 illustrates a generalized therapy delivery system 10 that may be used in spinal cord stimulation (SCS), as well as other stimulation applications. The therapy delivery system 10 generally includes an implantable pulse generator 12, an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded from as a uni-body construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 20.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 are protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
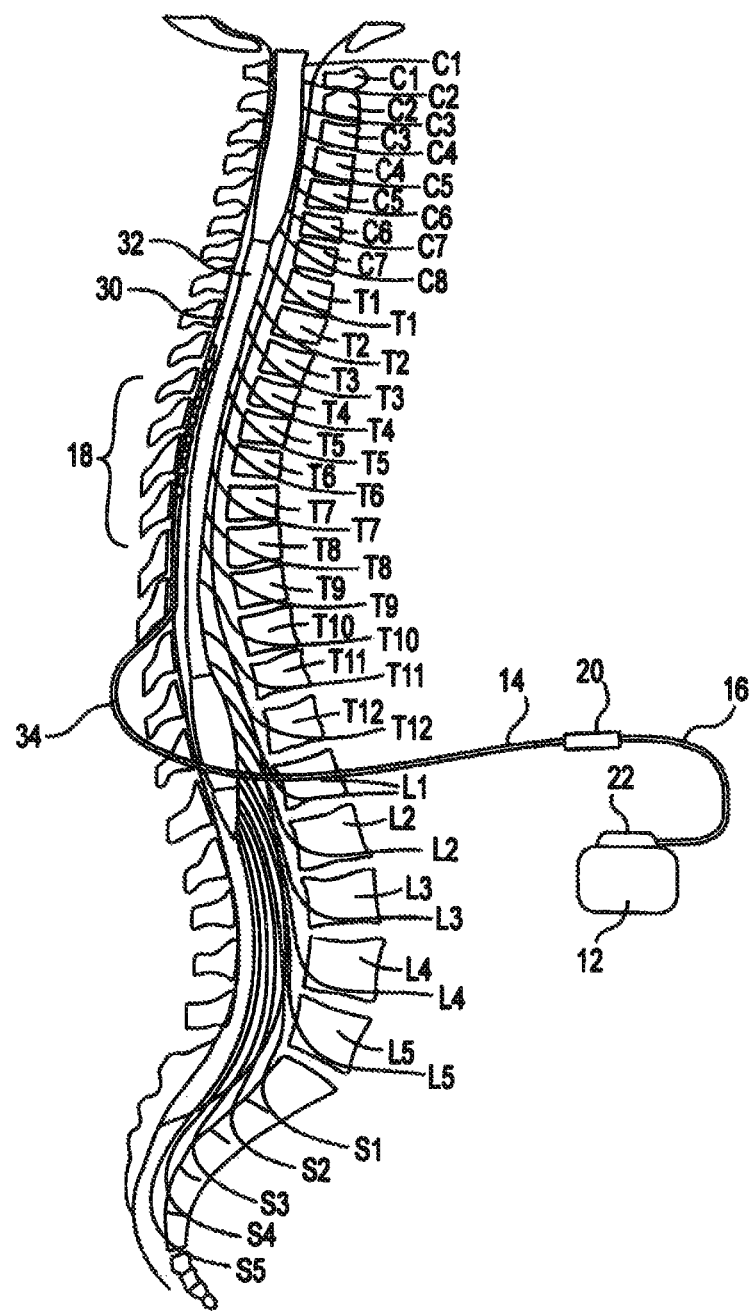
FIG. 2 is a schematic illustration of an environment for a therapy delivery system in accordance with an embodiment of the present disclosure.

FIG. 2 is a side skeletal view of a human body illustrating spinal column. The sacrum region is at a lower end of the spinal column below L-5 and adjacent the pelvic region. The sacrum is a triangular-shaped bone formed generally by five fused vertebrae, i.e., sacral vertebrae that are wedged dorsally between the two hip bones of the pelvic region in this region of the human anatomy. The lumbar region extends from L-1 to L-5 between the sacrum region at a lower end and the thorax region (T-1 to T-12) at an upper end. The thorax region extends from T-12 to T-1 at the base of the cervical region. The cervical region extends from C1 to C7.

The therapy delivery element 14 is implanted in the epidural space 30 of a patient in close proximity to the dura, the outer layer that surrounds the spinal cord 32, to deliver the intended therapeutic effects of spinal cord electrical stimulation. The target stimulation sites 49 (see e.g., FIG. 3) may be anywhere along the spinal cord 32, such as for example proximate the sacral nerves.

Figure 3:
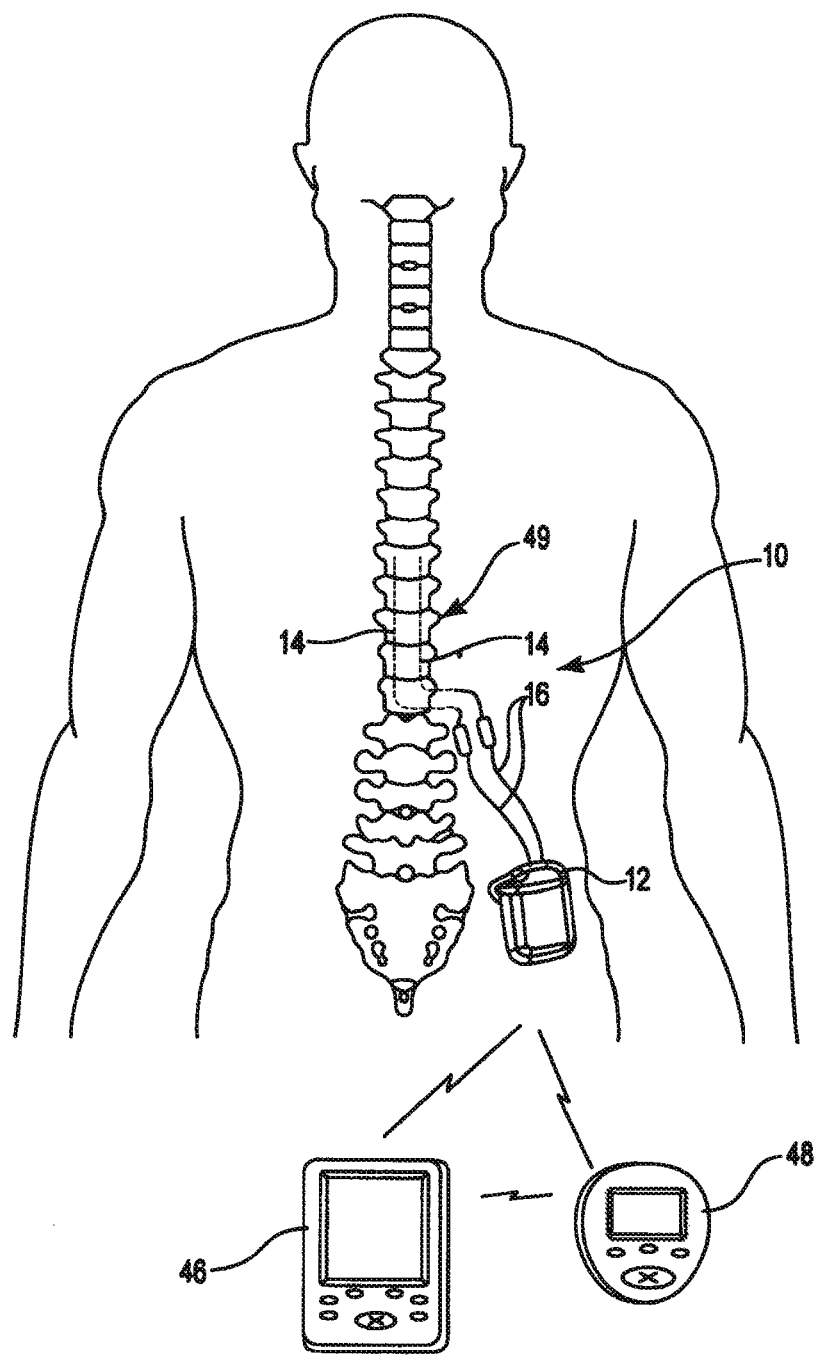
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 48, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Figure 4A:
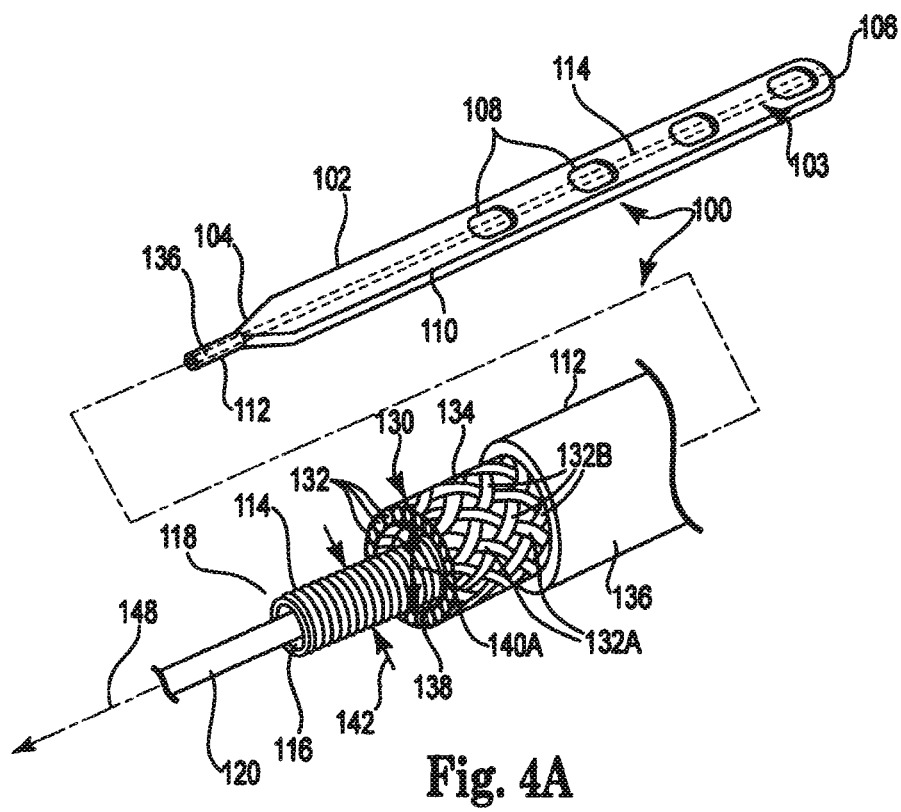
FIG. 4A is a schematic illustration of a paddle-style therapy delivery element in accordance with an embodiment of the present disclosure.

FIG. 4A is schematic illustration of a paddle-style therapy delivery element 100 in accordance with an embodiment of the present disclosure. The therapy delivery element 100 includes an electrode portion 102 having proximal end 104 and distal end 106, and a plurality of electrodes 108. In the illustrated embodiment, the electrode portion 102 is a generally round or tubular paddle structure. A variety of other electrode portions can be used with the present disclosure, such as disclosed in U.S. Pat. No. 6,978,180, which is incorporated by reference. In one embodiment, the electrode portions 102, 158, 260 disclosed herein are constructed from a polymeric material, such as for example, polyurethane or silicone, or an alloy of silicone and polyurethane, having a durometer in a range of about 20 Shore A to about 90 Shore A, as measured according to ASTM D2240.

The electrodes 108 may be recessed relative to surface 110 of the electrode portion 102 or are co-planar with the surface 110. Examples include recessing the electrode 0.010 inches (0.25 mm) from the surface 110 with the electrode portion 102. The electrode portion 102 may have a nominal length of about 8 inches (20 cm), nominal width of about 0.15 inches (3.8 mm), and a nominal thickness of about 0.04 inches (1 mm). The electrode portion 102 may be formed, for example, of material including polyurethane.

The electrode portion 102 may include one or more discrete radio-opaque markers 103. When fluoroscopically viewing a therapy delivery element 100, the orientation of the electrode portion 102 may be determined by noting on which side of the imaginary center line the orientation marker 103 appears to be positioned. In an exemplary embodiment, the orientation marker 103 may comprise radio-opaque material arranged in an asymmetric manner with respect to the width of the electrode portion 102.

The proximal end 104 of the electrode portion 102 preferably tapers down to the diameter of elongated lead body 112. The detailed illustration of the elongated lead body 112 is enlarged for clarity. The elongated lead body 112 includes stylet coil 114 with lumen 116. The stylet coil 114 and lumen 116 preferably extend from proximal end 118 of the elongated lead body 112 to distal end 106 of the electrode portion 102. The lumen 116 is sized to receive stylet 120.

The stylet coil 114 is preferably a helical coil of an elastically deformable material, such as for example, metal or a polymeric material. In one embodiment, the stylet coil 114 is a helical wire with a rectangular cross section, formed from polyurethane, polysulfone, polypropylene, or PEEK. The helically coiled structure separates between adjacent turns to allow stylet coil 114 to bend, either at a corner or during compression, while maintaining a substantially round cross-section. A metal stylet coil 114 is able to substantially withstand crushing and collapse by preventing cross-sectional flattening and forcing a larger bend radius than traditional plastic stylet guides.

In one embodiment, the stylet coil 114 is made from a wire with a diameter of about 0.012 inches to about 0.01 inches. In another embodiment, a metal stylet coil 114 is insulated with a polymer, such as ethylene-tetrafluoroethylene (ETFE), polytetrafluoroethylene (PTFE), modified PTFE, and polyimide, polyurethane, silicone, or polyester. In one embodiment, the stylet coil 114 is electrically inactive. Alternatively, the stylet coil 114 can carry signals or acts as a ground plane for the electrodes 108.

The stylet 120 provides steerability and rigidity, while the stylet coil 114 provides column strength to both the electrode portion 102 and the elongated lead body 112 to facilitate insertion and removal of the therapy delivery element 100 from a living body. The stylet coil 114 protects the electrode portion 102 and conductor assembly 130 during insertion and removal of the stylet 120. In some embodiments, the stylet 120 can include one or more bends that steer or direct the more flexible elongated lead portion 112 and electrode portion 102 to the target location. The stylet coil 114 also increases resistant to flex fatigue, buckling fatigue, axial displacement, kinking and crush, of the elongated lead body 112, while still permitting elongation or stretch of the elongated lead body 112.

Conductor assembly 130 extends through elongated lead body 112 to at least the proximal end 104 of the electrode portion 102. The conductor assembly 130 includes a plurality of electrical conductors 132 arranged in a tubular, braided configuration 134. In the illustrated embodiment, the conductor assembly 130 is a 2-over/2-under braid. Various other braid structures are disclosed in U.S. Pat. Publication No. 2008/0210328 (Henry), which is hereby incorporated by reference.

In one embodiment, the electrical conductors 132 are fluoropolymer insulated 0.005 diameter MP35N wires, which is a biocompatible, nonmagnetic, nickel-cobalt-chromium-molybdenum alloy with high strength and corrosion resistance, with gold or silver cores to improve conductance.

Low durometer insulator 136 extends around the conductor assembly 130. The insulator 136 can be an extruded or molded material, such as for example, polyurethane or silicone, or an alloy of silicone and polyurethane. In one embodiment, the insulators 136 of elongated lead bodies 112, 160, 258, 320 disclosed herein have a durometer in a range of about 55 Shore A to about 75 Shore A, and alternatively about 30 Shore A to about 60 Shore A, as measured according to ASTM D2240.

In one embodiment, the electrical conductors 132A are braided with non-conductive elements 132B. In the preferred embodiment, the electrical conductors 132A are all oriented generally parallel within the braided structure, and the non-conductive elements 132B are oriented in the other direction. Consequently, the electrical conductors 132A do not cross over each other.

The electrical conductors 132 are electrically coupled to the electrodes 108 in a manner known in the art. In one embodiment, the braided configuration 134 terminates at the proximal end 104 of the electrode portion 102, and the individual electrical conductors 132 continue through the electrode portion 102 to the electrodes 108. In another embodiment, the braided portion continues along the stylet coil 114 for all or a portion of the length of the electrode portion 102.

The braided configuration 134 is a complex structure or pattern formed by intertwining the electrical conductors 132. Each electrical conductor 132 is preferably functionally equivalent in zigzagging forward through the overlapping mass of the other conductors 132. The braided configuration 134 preferably includes lumen 138 that preferably has an inside diameter 140A greater than outside diameter 142 of the stylet coil 114. Consequently, gap 144 permits the braided configuration 134 to neck-down during elongation or stretching of the conductor assembly 130. In one embodiment, the conductor assembly 130 is not attached to the stylet coil 114, except at the proximal ends 104, 118. In relaxed configuration 146 illustrated in FIG. 4A, the individual electrical conductors 132 are oriented at an angle of about 20 degrees to about 45 degrees relative to central axis 148 of the elongated lead body 112.

Figure 4B:
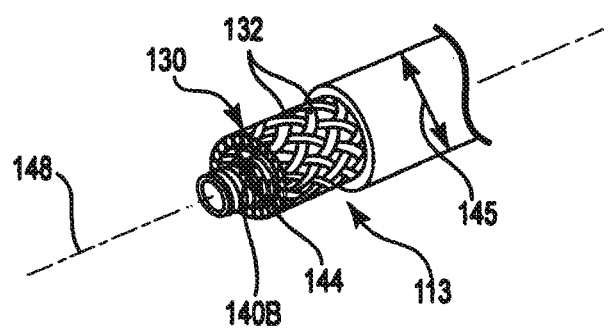
FIG. 4B is a schematic illustration of an elongated lead body of FIG. 4A in an elongated configuration in accordance with an embodiment of the present disclosure.

FIG. 4B illustrates the elongated lead body 112 in an elongated configuration 113. During elongation the conductor assembly 130 necks down to a smaller diameter 140B, permitting an increase in overall length of the elongated lead body 112 (see, e.g., FIG. 9), without damaging the individual conductors 132. In particular, the individual conductors 132 rotate toward alignment with central axis 148 of the elongated lead body 112. In the elongated configuration 113, the individual conductors 132 form an angle with the central axis 148 of about 0 degrees to about 25 degrees. The gap 144 is reduced or eliminated. In the illustrated embodiment, outside diameter 145 of the insulator 136 also decreases in the elongated configuration 113.

The braided configuration 134 permits the conductor assembly 130 to elongate under tension, without damaging the individual electrical conductors 132. Elongation of the conductor assembly 130 reduces mechanical loading on tissue anchor points, implantable lead extensions 16, the implantable therapy delivery element 100, and the implantable pulse generator 12 during typical patient movement. In addition, the braided configuration 134 lead may improve resistance to flex fatigue, buckling fatigue, kinking, and crush.

The braided configuration 134 exhibits reduced axial stiffness. The target axial stiffness may be achieved by selection of appropriate materials, insulator 136, and braid configuration 134 for the electrical conductors 132. A reduced axial stiffness in the above range promotes increased stretchability in the elongated lead body 112 to better accommodate changes in length along the patient's body. In some cases, the enhanced stretchability may substantially eliminate lead failure due to fractures or electrical shorting, axial migration of electrodes coupled to the lead body, anchor damage, and/or tissue damage at anchor points.

Figure 5:
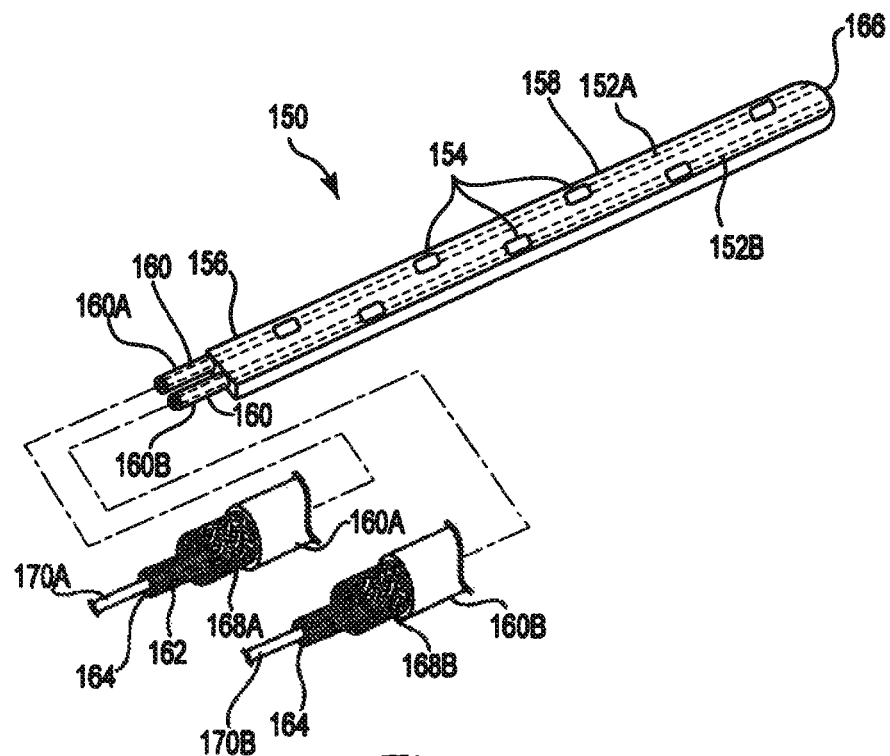
FIG. 5 is a schematic illustration of an alternate paddle-style therapy delivery element in accordance with an embodiment of the present disclosure.

FIG. 5 is schematic illustration of an alternate paddle-style therapy delivery element 150 with a plurality of rows 152A, 152B of electrodes 154, in accordance with an embodiment of the present disclosure. Proximal end 156 of electrode portion 158 includes a pair of elongated lead bodies 160A, 160B ("160"). The detailed illustration of the elongated lead bodies 160 are enlarged for clarity. Each elongated lead body 160 includes stylet coil 162 with lumen 164 that extends to distal end 166 of electrode portion 158. Braided electrical conductors 168A, 168B are electrically coupled to row 152A, 152B of the electrodes 154, respectively, as discussed above. Stylets 170A, 170B can be used simultaneously to steer the therapy delivery element 150 to the desired location in the patient.

Figure 6:
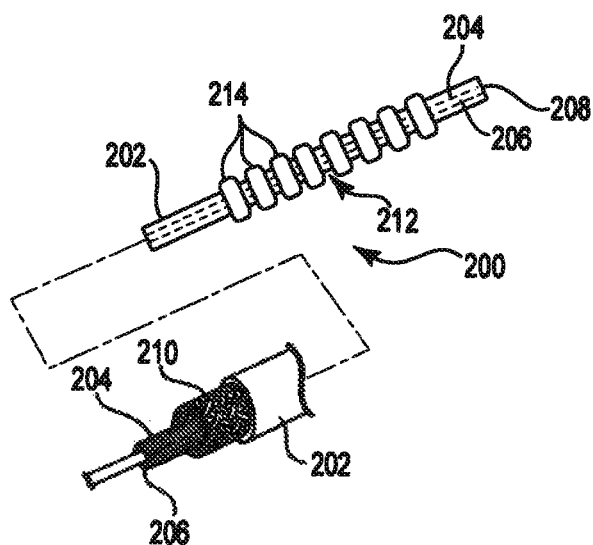
FIG. 6 is a schematic illustration of a ring electrode-style therapy delivery element lead in accordance with an embodiment of the present disclosure.

FIG. 6 is a schematic illustration of a ring-electrode therapy delivery element 200 with an electrode portion 212 and an elongated lead body 202 in accordance with an embodiment of the present disclosure. The electrode portion 212 include a plurality of ring-electrodes 214. The stylet coil 204 and associated lumen 206 preferably extend to distal end 208 of the therapy delivery element 200. Braided electrical conductors 210 are extend around the stylet coil 204, substantially as discussed above.

Figure 7:
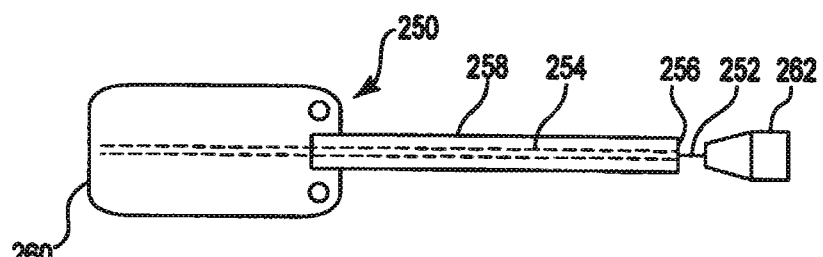
FIG. 7 is a schematic illustration of a method of implanting a therapy delivery element in accordance with an embodiment of the present disclosure.
Figure 9:
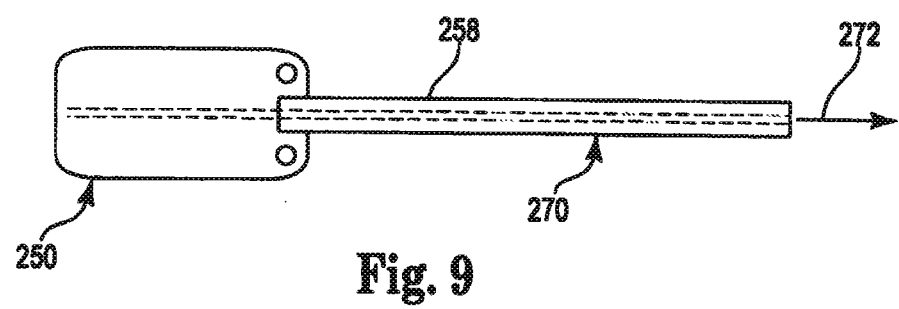
FIG. 9 is a schematic illustration of the therapy delivery element of FIG. 7 in an elongated configuration in accordance with an embodiment of the present disclosure.
Figure 8:
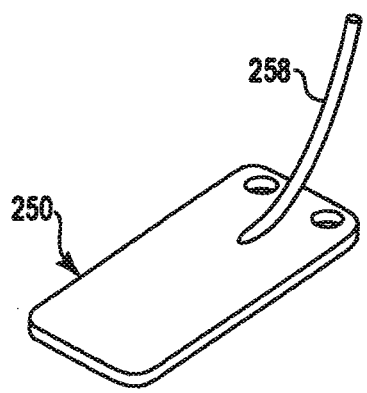
FIG. 8 is a schematic illustration of the therapy delivery element of FIG. 7 after implantation in accordance with an embodiment of the present disclosure.

FIGS. 7 through 9 are schematic illustrations of a method of implanting a therapy delivery element 250 in accordance with an embodiment of the present disclosure. Stylet 252 is inserted in lumen of stylet coil 254. In the illustrated embodiment, the stylet 252 extends from the proximal end 256 of the elongated lead body 258 to the distal end 260 of the therapy delivery element 250. The elongated lead body 258 includes a conductor assembly with braided electrical conductors as discussed herein (see e.g., FIG. 4).

The physician grasps the elongated lead body 258 and/or stylet hub 262 to steer the therapy delivery element 250 to the desired location in the living body. The stylet 252 provides stiffness to the elongated lead body 258, while the stylet coil 254 provides column strength. Once properly located within the living body, the stylet 252 is removed. As illustrated in FIG. 8, the elongated lead body 258 is now highly flexible and stretchable. As illustrated in FIG. 9, the elongated lead body 258 is in stretched configuration 270, resulting from tension force 272 created within the living body. During stretching, the braided conductors necks down to provide increase overall length of the conductor assembly, without damaging the individual conductors.

Figure 10:
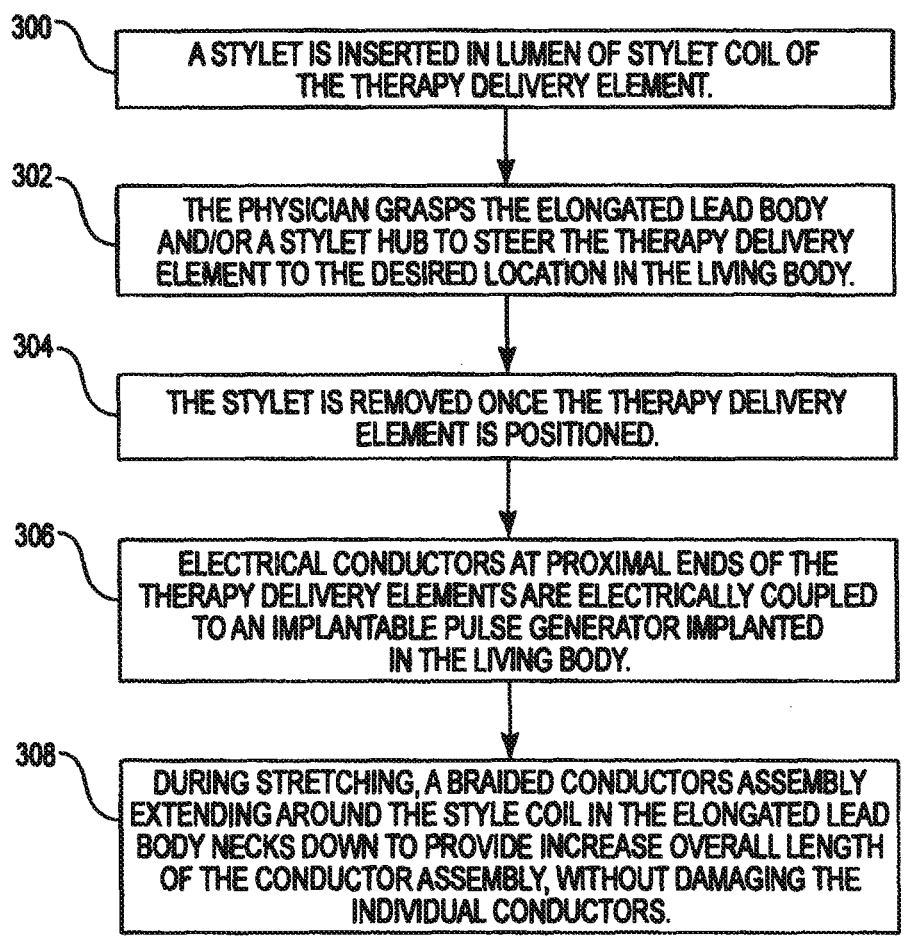
FIG. 10 is a flow diagram of a method of implanting therapy delivery elements in an epidural space using an epidural needle in accordance with an embodiment of the present disclosure.

FIG. 10 is a flow diagram of a method of implanting a neurostimulation system within a living body in accordance with an embodiment of the present disclosure. A stylet is inserted in lumen of stylet coil of the therapy delivery element (300). The physician grasps the elongated lead body and/or a stylet hub to steer the therapy delivery element to the desired location in the living body (302). The stylet is removed once the therapy delivery element is positioned (304). Proximal ends of the therapy delivery elements are electrically coupled to an implantable pulse generator implanted in the living body (306). During stretching, a braided conductors assembly extending around the style coil in the elongated lead body necks down to provide increase overall length of the conductor assembly, without damaging the individual conductors (308).

Figure 11:
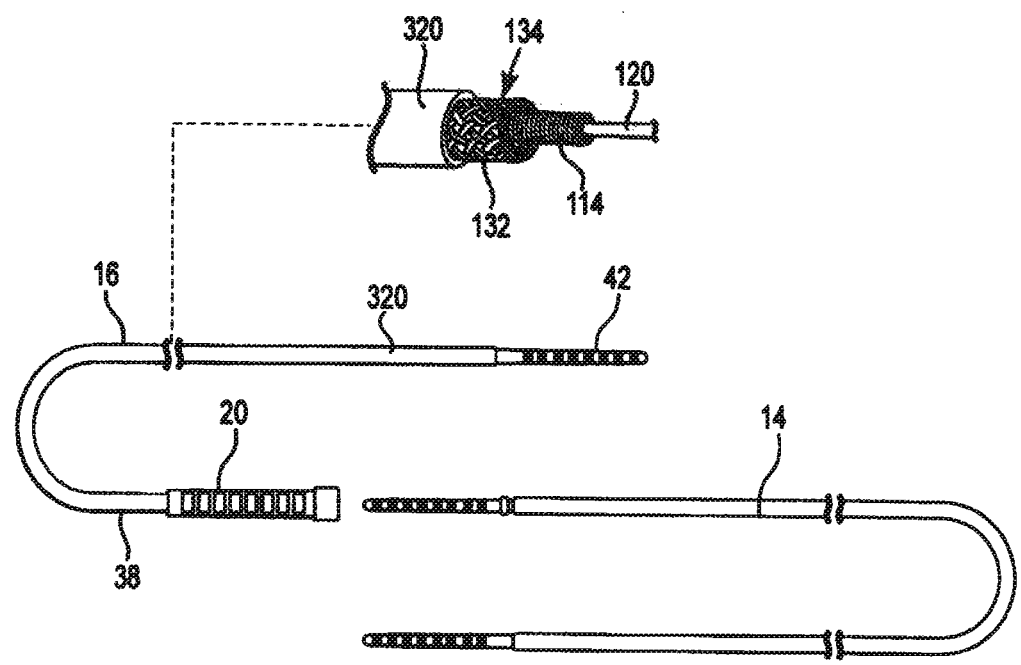
FIG. 11 is a lead extension for a therapy delivery element in accordance with an embodiment of the present disclosure.

FIG. 11 illustrates an embodiment of lead extension 16 (illustrated in FIG. 1) with a plurality of braided electrical conductors in accordance with an embodiment of the present disclosure. The distal end 38 of the lead extension 16 includes connector 20 and proximal end 42 includes contact rings that electrically couple with connector 22.

Elongated lead body 320 includes a plurality of the electrical conductors 132 arranged in a tubular, braided configuration 134. The stylet coil 114 may optionally be included in the elongated lead body 320 in order to receive stylet 120 for certain applications. Alternatively, the stylet coil 114 and stylet 120 may be omitted for some applications.

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. An extension for a therapy delivery element configured to be implanted into a living body, the extension comprising:
   a distal connector configured to electrically couple to a proximal end of the therapy delivery element;
   an extension body attached to the connector, the extension body including:
      a stylet coil including a stylet coil lumen, the stylet coil extending within the extension body to the connector;
      a conductor assembly including a plurality of insulated electrical conductors braided in a tubular braided configuration around the stylet coil and electrically coupled to the connector, the tubular braided configuration including the plurality of insulated electrical conductors braided with one another, the conductor assembly including an inner lumen with a diameter greater than an outside diameter of the stylet coil, wherein the inner lumen of the conductor assembly is separated from the stylet coil by a gap with the extension body in a relaxed condition, wherein axial elongation of the extension body reduces an inner diameter of the conductor assembly to close the gap and cause the conductor assembly to constrict around the stylet coil; and
      a low durometer insulator extending around the conductor assembly; and
   a stylet sized to slide freely within the stylet coil lumen during implantation of the extension with respect to the living body.

2. The extension of claim 1, wherein the plurality of insulated electrical conductors are braided with non-conductive elements to form the tubular braided configuration, the plurality of insulated electrical conductors being oriented substantially parallel to each other, and the non-conductive elements are oriented substantially parallel to each other but not parallel to the plurality of insulated electrical conductors.

3. The extension of claim 1, wherein the plurality of insulated electrical conductors, in an elongated configuration, includes the plurality of insulated electrical conductors displaced toward alignment with a central axis of the extension body.

4. The extension of claim 1, wherein the axial elongation of the extension body results from elongation of the tubular braided configuration and not from elongation of individual insulated electrical conductors of the plurality of insulated electrical conductors.

5. The extension of claim 1, wherein the extension body has an axial stiffness that permits an axial elongation of at least 10 percent to 35 percent, without breakage of the plurality of insulated electrical conductors.

6. The extension of claim 1, comprising a proximal connector configured to electrically couple to an implantable pulse generator.

7. The extension of claim 1, comprising a proximal connector configured to electrically couple to a distal connector of another extension.

8. An extension for a therapy delivery element configured to be implanted into a living body, the extension comprising an extension body including:
   a stylet coil including a stylet coil lumen, the stylet coil extending within the extension body, the stylet coil being configured to accept a stylet within the stylet coil lumen during implantation of the extension with respect to the living body;
   a conductor assembly including a plurality of insulated electrical conductors braided in a tubular braided configuration around the stylet coil, the tubular braided configuration including the plurality of insulated electrical conductors braided with one another, the conductor assembly including an inner lumen with a diameter greater than an outside diameter of the stylet coil, wherein the inner lumen of the conductor assembly is separated from the stylet coil by a gap with the extension body in a relaxed condition, wherein, with axial elongation, the extension body, in an elongated configuration, includes a reduced inner diameter of the conductor assembly, the reduced inner diameter being smaller than an inner diameter of the conductor assembly with the extension body in the relaxed configuration, the axial elongation of the extension body closing the gap and causing the conductor assembly to constrict around the stylet coil, the axial elongation of the extension body resulting from elongation of the tubular braided configuration and not from elongation of individual insulated electrical conductors of the plurality of insulated electrical conductors, wherein the conductor assembly:
      in the relaxed configuration, is spaced from the stylet coil; and
      in the elongated configuration, includes the electrical conductor displaced toward alignment with a central axis of the extension body; and
   a low durometer insulator extending around the conductor assembly.

9. The extension of claim 8, wherein the plurality of insulated electrical conductors are braided with non-conductive elements to form the tubular braided configuration, the plurality of insulated electrical conductors being oriented substantially parallel to each other, and the non-conductive elements are oriented substantially parallel to each other but not parallel to the plurality of insulated electrical conductors.

10. The extension of claim 8, comprising a distal connector configured to electrically couple to a proximal end of the therapy delivery element.

11. The extension of claim 8, comprising a distal connector configured to electrically couple to a proximal end of another extension.

12. The extension of claim 8, comprising a proximal connector configured to electrically couple to an implantable pulse generator.

13. The extension of claim 8, comprising a proximal connector configured to electrically couple to a distal connector of another extension.

14. The extension of claim 8, wherein the axial elongation of the extension body results from elongation of the tubular braided configuration and not from elongation of individual insulated electrical conductors of the plurality of insulated electrical conductors.

15. An extension for a therapy delivery element configured to be implanted into a living body, the extension comprising at least one extension body including:
   a stylet coil including a stylet coil lumen, the stylet coil extending within the extension body;
   a conductor assembly including a plurality of insulated electrical conductors braided with one another in a tubular braided configuration around the stylet coil and electrically coupled to one or more of the electrodes, the conductor assembly including an inner lumen having an unelongated inner diameter that is greater than an outside diameter of the stylet coil with the conductor assembly in an unelongated configuration, the inner lumen of the conductor assembly being separated from the stylet coil by a gap with the conductor assembly in the unelongated configuration, wherein axial elongation of the conductor assembly of the extension body into an elongated configuration provides an elongated inner diameter of the conductor assembly that is less than the unelongated inner diameter to close the gap and cause the conductor assembly to constrict around the stylet coil; and
   a low durometer insulator extending around the conductor assembly, wherein the stylet coil lumen provides for free movement of a stylet therethrough during implantation of the extension with respect to the living body with the conductor assembly in either the unelongated configuration or the elongated configuration.

16. The extension of claim 15, wherein the axial elongation of the conductor assembly results from elongation of the tubular braided configuration and not from elongation of individual insulated electrical conductors of the plurality of insulated electrical conductors.

17. The extension of claim 15, wherein the plurality of insulated electrical conductors are braided with non-conductive elements to form the tubular braided configuration, the plurality of insulated electrical conductors being oriented substantially parallel to each other, and the non-conductive elements are oriented substantially parallel to each other but not parallel to the plurality of insulated electrical conductors.

18. The extension of claim 15, comprising a distal connector configured to electrically couple to a proximal end of the therapy delivery element or a proximal end of another extension.

19. The extension of claim 15, comprising a proximal connector configured to electrically couple to an implantable pulse generator or a distal connector of another extension.

20. The extension of claim 15, wherein the plurality of insulated electrical conductors, in the elongated configuration, includes the plurality of insulated electrical conductors displaced toward alignment with a central axis of the extension body.

* * * * *